US009029426B2

(12) United States Patent
Markosyan et al.

(10) Patent No.: US 9,029,426 B2
(45) Date of Patent: May 12, 2015

(54) HIGHLY SOLUBLE REBAUDIOSIDE D

(75) Inventors: Avetik Markosyan, Yerevan (AM);
Siddhartha Purkayastha, Lombard, IL (US)

(73) Assignee: PureCircle Sdn Bhd, Negeri Sembilan (MY)

( * ) Notice: Subject to any disclaimer, the term of this patent is extended or adjusted under 35 U.S.C. 154(b) by 68 days.

(21) Appl. No.: 13/993,415

(22) PCT Filed: Dec. 12, 2011

(86) PCT No.: PCT/US2011/064343
§ 371 (c)(1),
(2), (4) Date: Jun. 12, 2013

(87) PCT Pub. No.: WO2012/082587
PCT Pub. Date: Jun. 21, 2012

(65) Prior Publication Data
US 2013/0274351 A1 Oct. 17, 2013

Related U.S. Application Data

(60) Provisional application No. 61/422,403, filed on Dec. 13, 2010, provisional application No. 61/424,798, filed on Dec. 20, 2010.

(51) Int. Cl.
A61K 47/00 (2006.01)
A23L 1/236 (2006.01)
A23L 2/60 (2006.01)
C07H 15/24 (2006.01)
C07H 1/08 (2006.01)

(52) U.S. Cl.
CPC ............ *A23L 1/2363* (2013.01); *A23L 1/2364* (2013.01); *A23L 1/2366* (2013.01); *A23L 2/60* (2013.01); *C07H 15/24* (2013.01); *C07H 1/08* (2013.01)

(58) Field of Classification Search
USPC ........................................................ 514/777
See application file for complete search history.

(56) References Cited

U.S. PATENT DOCUMENTS

| 3,723,410 | A | 3/1973 | Persinos |
| 4,082,858 | A | 4/1978 | Morita et al. |
| 4,171,430 | A | 10/1979 | Matsushita et al. |
| 4,219,571 | A | 8/1980 | Miyake |
| 4,361,697 | A | 11/1982 | Dobberstein et al. |
| 4,454,290 | A | 6/1984 | Dubois |
| 4,590,160 | A | 5/1986 | Nishihashi et al. |
| 4,599,403 | A | 7/1986 | Kumar |
| 4,612,942 | A | 9/1986 | Dobberstein et al. |
| 4,657,638 | A | 4/1987 | le Grand et al. |
| 4,892,938 | A | 1/1990 | Giovanetto |
| 4,917,916 | A | 4/1990 | Hirao et al. |
| 5,112,610 | A | 5/1992 | Kienle |
| 5,576,042 | A | 11/1996 | Fuisz |
| 5,779,805 | A | 7/1998 | Morano |
| 5,962,678 | A | 10/1999 | Payzant et al. |
| 5,972,120 | A | 10/1999 | Kutowy et al. |
| 6,031,157 | A | 2/2000 | Morita et al. |
| 6,080,561 | A | 6/2000 | Morita et al. |
| 6,204,377 | B1 | 3/2001 | Nishimoto et al. |
| 6,228,996 | B1 | 5/2001 | Zhou et al. |
| 6,706,304 | B1 | 3/2004 | Ishida et al. |
| 7,807,206 | B2 | 10/2010 | Magomet et al. |
| 7,838,044 | B2 | 11/2010 | Abelyan et al. |
| 7,862,845 | B2 | 1/2011 | Magomet et al. |
| 8,257,948 | B1 | 9/2012 | Markosyan |
| 2002/0132320 | A1 | 9/2002 | Wang et al. |
| 2003/0161876 | A1 | 8/2003 | Hansson et al. |
| 2003/0236399 | A1 | 12/2003 | Zheng et al. |
| 2006/0083838 | A1 | 4/2006 | Jackson et al. |
| 2006/0134292 | A1 | 6/2006 | Abelyan et al. |
| 2006/0142555 | A1 | 6/2006 | Jonnala et al. |
| 2007/0082102 | A1 | 4/2007 | Magomet et al. |
| 2007/0082103 | A1 | 4/2007 | Magomet et al. |
| 2007/0116800 | A1 | 5/2007 | Prakash |
| 2007/0116819 | A1 | 5/2007 | Prakash |
| 2007/0116820 | A1 | 5/2007 | Prakash |
| 2007/0116821 | A1 | 5/2007 | Prakash |
| 2007/0116822 | A1 | 5/2007 | Prakash |
| 2007/0116823 | A1 | 5/2007 | Prakash |
| 2007/0116824 | A1 | 5/2007 | Prakash |
| 2007/0116825 | A1 | 5/2007 | Prakash |

(Continued)

FOREIGN PATENT DOCUMENTS

BR P10701736 7/2008
CN 1049666 3/1991

(Continued)

OTHER PUBLICATIONS a-Glucosyltransferase Treated Stevia, Japan's Specifications and Standards for Food Additives, VIII edition, 2009, p. 257.
Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S. S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside A from stevia glycosides by a novel adsorbent with pyridyl group", Science in China, vol. 42, No. 3 1999, 277-282.

(Continued)

Primary Examiner — Shirley V Gembeh
(74) Attorney, Agent, or Firm — Briggs and Morgan, P.A.; Aleya R. Champlin; Audrey J. Babcock

(57) ABSTRACT

The invention relates to a process for producing highly soluble compositions containing purified steviol glycosides from *Stevia rebaudiana* Bertoni plant extract, more particularly Rebaudioside D. Obtained highly soluble compositions are useful as non-caloric sweeteners or in combination with sugar or high intensity sweeteners in edible and chewable compositions such as beverages, confectionaries, bakery products, chewing gums and the like.

12 Claims, 1 Drawing Sheet

(56) References Cited

U.S. PATENT DOCUMENTS

| | | |
|---|---|---|
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi et al. |
| 2008/0226797 A1 | 9/2008 | Lee et al. |
| 2008/0292764 A1 | 11/2008 | Prakash et al. |
| 2008/0292765 A1 | 11/2008 | Prakash |
| 2008/0292775 A1 | 11/2008 | Prakash |
| 2008/0300402 A1 | 12/2008 | Yang et al. |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris et al. |
| 2009/0142817 A1 | 6/2009 | Norman et al. |
| 2009/0226590 A1 | 9/2009 | Fouache et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0112153 A1 | 5/2010 | Abelyan et al. |
| 2010/0120710 A1 | 5/2010 | Watanabe et al. |
| 2010/0137569 A1 | 6/2010 | Prakash et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0316782 A1 | 12/2010 | Shi et al. |
| 2011/0030457 A1 | 2/2011 | Valery et al. |
| 2011/0033525 A1 | 2/2011 | Lui |
| 2011/0092684 A1 | 4/2011 | Abelyan et al. |
| 2011/0104353 A1 | 5/2011 | Lee |
| 2011/0111115 A1 | 5/2011 | Shi et al. |
| 2011/0124587 A1 | 5/2011 | Jackson et al. |
| 2011/0160311 A1 | 6/2011 | Prakash et al. |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |

FOREIGN PATENT DOCUMENTS

| | | |
|---|---|---|
| CN | 1100727 | 3/1995 |
| CN | 1112565 | 11/1995 |
| CN | 1192447 | 9/1998 |
| CN | 1238341 | 12/1999 |
| CN | 1349997 | 5/2002 |
| CN | 101200480 | 6/2008 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 62166861 | 7/1987 |
| JP | 63173531 | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | 2005089483 | 9/2005 |
| WO | 2006072878 | 7/2006 |
| WO | 2006072879 | 7/2006 |
| WO | WO 2007/061795 | * 5/2007 |
| WO | 2008091547 | 7/2008 |
| WO | 2009108680 | 9/2009 |
| WO | WO2010057024 | 5/2010 |
| WO | 2010118218 | 10/2010 |
| WO | 2011059954 | 5/2011 |
| WO | 2011153378 | 12/2011 |
| WO | 2012082493 | 6/2012 |
| WO | 2012082677 | 6/2012 |
| WO | 2013022989 | 2/2013 |

OTHER PUBLICATIONS

Chen, et al., "Selectivity of polymer adsorbent in adsorptive separations of stevia diterpene glycisides", Science in China, vol. 41, No. 4 1998, 436-441.

Chen, et al., "Studies on the adsorptive selectivity of the polar resin with carbonyl group on rebaudioside A", Acta Polymeric Scnica, No. 4 1999, 398-403.

Crammer, et al., "Sweet glycosides from the Stevia plant", Chemistry in Britain, Oct. 1986, 915-916, 918.

Darise et al., "Enzymic Transglucosylation of Rubusoside and the Structure-Sweetness Relationship of Steviol Bisglycosides," Agric. Biol. Chem. vol. 48(10), 1984, 2483-2488.

Dubois et al., "Diterpenoid Sweeteners. Synthesis and Sensory Evaluation of Stevioside Analogues with Improved Organoleptic Properties," J. Med. Chem. vol. 28, (1985) 93-98.

Fuh, , "Purification of steviosides by membrane and ion exchange process", Journal of Food Science, vol. 55, No. 5 1990, 1454-1457.

(56) References Cited

OTHER PUBLICATIONS

Fukunaga et al., "Enzymic Transglucosylation Products of Stevioside: Separation and Sweetness-evaluation," Agric. Biol. Chem. vol. 53(6) (1989) 1603-1607.
Fullas et al., "Separation of natural product sweetening agents using overpressured layer chromatography," Journal of Chromatography vol. 464 (1989) 213-219.
Hale, et al., "Amylase of *Bacillus macerans*", Cereal Chemistry, vol. 28, No. 1, Jan. 1951, 49-58.
International Search Report and Written Opinion of PCT/US2010/055960.
International Search Report and Written Opinion of PCT/US2011/028028.
International Search Report and Written Opinion of PCT/US2011/033734.
International Search Report and Written Opinion of PCT/US2011/033737.
International Search Report and Written Opinion of PCT/US2011/033912.
International Search Report and Written Opinion of PCT/US2011/035173.
International Search Report and Written Opinion of PCT/US2011/036063, mailed Aug. 5, 2011.
International Search Report and Written Opinion of PCT/US2011/047498, mailed Dec. 22, 2011.
International Search Report and Written Opinion of PCT/US2011/047499, mailed Dec. 22, 2011.
International Search Report and Written Opinion of PCT/US2011/064343.
International Search Report and Written Opinion of PCT/US2012/024585.
International Search Report and Written Opinion of PCT/US2012/024722.
International Search Report and Written Opinion of PCT/US2012/030210.
International Search Report and Written Opinion of PCT/US2012/043294.
International Search Report and Written Opinion of PCT/US2012/051163.
International Search Report and Written Opinion of PCT/US2012/052659.
International Search Report and Written Opinion of PCT/US2012/052665.
International Search Report and Written Opinion of PCT/US2013/030439.
Jaitak, et al., "An Efficient Microwave-assisted Extraction Process of Stevioside and Rebaudioside-A from *Stevia rebaudiana* (Bertoni)", Phytochem. Anal. vol. 20 2009, 240-245.
Kennelly, "Sweet and non-sweet constituents of *Stevia rebaudiana*", Stevia: The genus Stevia, Taylor & Francis, 2002, 68-85.
Kinghorn, "Overview", Stevia: The genus Stevia, Taylor & Francis, 2002, 1-17.
Kitahata, S. et al., "Production of Rubusoside Derivatives by Transgalactosylation of Various b-Galactosidases", Agric. Biol. Chem., vol. 53, No. 11 1989, 2923-2928.
Kobayashi, et al., "Dulcoside A and B, New diterpene glycosides from *Stevia rebaudiana*", Phytochemistry, vol. 16 1977, 1405-1408.
Kochikyan, et al., "Combined Enzymatic Modification of Stevioside and Rebaudioside A", Applied Biochemistry and Microbiology, vol. 42, No. 1, 2006, 31-37.
Kohda, et al., "New sweet diterpene glucosides from *Stevia rebaudiana*", Phytochemistry, vol. 15 1976, 981-983.
Kovylyaeva, et al., "Glycosides from *Stevia rebaudiana*", Chemistry of Natural Compounds, vol. 43, No. 1 2007, 81-85.
Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chem., vol. 55, No. 12 1991, 2959-2965.

Montovaneli, et al., "The effect of temperature and flow rate on the clarification of the aqueous Stevia-extract in fixed-bed column with zeolites", Brazilian Journal of Chemical Engineering, vol. 21, No. 3 2004, 449-458.
Moraes, et al., "Clarification of *Stevia rebaudiana* (Bert.) Bertoni extract adsorption in modified zeolites", Acta Scientiarum, vol. 23, No. 6 2001, 1375-1380.
Ohta et al., "Characterization of Novel Steviol Glycosides from Leaves of *Stevia rebaudiana* Morita," J. Appl. Glycosi., vol. 57, 199-209, 2010.
Ohtani et al. "Chapter 7. Methods to improve the taste of the sweet principles of *Stevia rebaudiana*." The Genus Stevia, edited by A. Douglas Kinghorn, CRC Press 2001, Taylor and Francis, London and New York, pp. 138-159.
Phillips, K. C., "Stevia: steps in developing a new sweetener", in T.H. Grenby, Editor, Developments in Sweeteners-3, Elsevier 1987, 1-43.
Pol, et al., "Comparison of two different solvents employed for pressurised fluid extraction of stevioside from *Stevia rebaudiana*: methanol versus water", Anal Bioanal Chem vol. 388 2007, 1847-1857.
Prakash et al., "Development of rebiana, a natural, non-caloric sweetener," Jul. 1, 2008, Food and Chemical Toxology, vol. 46, Is. 7, Sup. 1, p. S75-S82.
Richman et al., "Fuctional genomics uncovers three glucosyltransferases involved in the synthesis of the major sweet glucosides of *Stevia rebaudiana*," The Plant Journal, vol. 41 (2005) 56-67.
Sakamoto et al., "Application of 13C NMR Spectroscopy to Chemistry of Natural Glycosides: Rebaudioside-C, a New Sweet Diterpene Glycoside of *Stevia rebaudiana*", Chem. Pharm. Bull., vol. 25, 1977, 844-846.
Shi, et al., "Synthesis of bifunctional polymeric adsorbent and its application in purification of Stevia glycosides", Reactive & Functional Polymers, vol. 50 2002, 107-116.
Shibata et al., "Glucosylation of Steviol and Steviol-Glucosides in Extracts from *Stevia rebaudiana* Bertoni," Plant Physiol. vol. 95, (1991) 152-156.
Starratt, et al., "Rebaudioside F, a diterpene glycoside from *Stevia rebaudiana*", Phytochemistry, vol. 59 2002, 367-370.
Sweet Green Fields, LLC, "Notice to the U.S. Food and Drug Administration (FDA) that the use of Rebiana (Rebaudiosid A) derived from *Stevia rebaudiana*, as a Food Ingredient is Generally Recognized as Safe (GRAS)," Jan. 15, 2009, http:/www.accessdata.fda.gov/scripts/fcn/gras_notices/grn000282.pdf (obtained from the WEB on May 8, 2012) entire document esp. p. 22, Table 1.
Tanaka, O., "Improvement of taste of natural sweeteners", Pure & Appl. Chem., vol. 69, No. 4 1997, 675-683.
Teo, et al., "Validation of green-solvent extraction combined with chromatographic chemical fingerprint to evaluate quality of *Stevia rebaudiana* Bertoni", J. Sep. Sci, vol. 32 2009, 613-622.
United Nations' Food and Agriculture Organization/Joint Expert Committee on Food Additives (2010) Steviol Glycosides, Compendium of Food Additive Specifications, FAO JECFA Monographs 10, 17-21.
van der Maarel et al., "Properties and applications of starch-converting enzymes of the a-amylase family," Journal of Biotechnology, vol. 94 (2002) 137-155.
Vasquez, Stimulation of the Gerbil's Gustatory Receptors by Some Potently Sweet Terpenoids, J. Agric. Food Chem., vol. 41, 1305-1310, 1993.
Yamamoto, K. et al., "Effective Production of Glycosyl-steviosides by a-1,6 Transglucosylation of Dextrin Dextranase", Biosci. Biotech. Biochem. vol. 58, No. 9 1994, 1657-1661.
Yoda, et al., "Supercritical fluid extraction from *Stevia rebaudiana* Bertoni using CO2 and CO2+ water: extraction kinetics and identification of extracted components", Journal of Food Engineering, vol. 57 2003, 125-134.
Zell, et al., "Investigation of Polymorphism in Aspartame and Neotame Using Solid-State NMR Spectroscopy", Tetrahedron, vol. 56, 2000, 6603-6616.
Zhang, et al., "Membrane-based separation scheme for processing sweetener from Stevia leaves", Food Research International, vol. 33 2000, 617-620.

\* cited by examiner

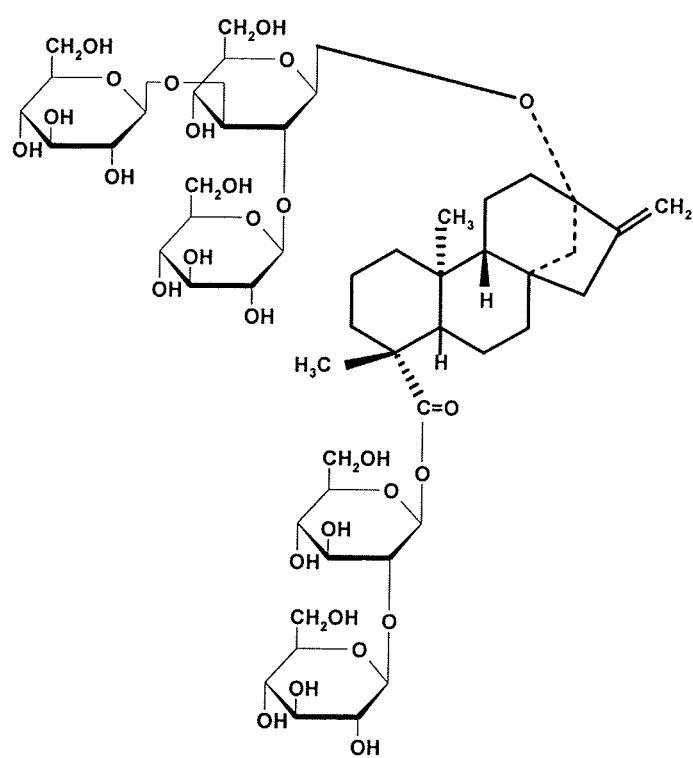
REBAUDIOSIDE D

HIGHLY SOLUBLE REBAUDIOSIDE D

PRIOR APPLICATION INFORMATION

This application is entitled to the earlier filing dates of, and claims the benefit of priority to, U.S. Provisional Application No. 61/422,403, filed on Dec. 13, 2010, and U.S. Provisional Application No. 61/424,798, filed on Dec. 20, 2010, the contents of which are incorporated by reference herein in their entirety.

FIELD OF THE INVENTION

The invention relates to a process for producing highly soluble compositions containing purified steviol glycosides from *Stevia rebaudiana* Bertoni plant extract, more particularly Rebaudioside D.

BACKGROUND OF THE INVENTION

High intensity sweeteners possess a sweetness level many times exceeding that of sucrose. They are essentially non-caloric and used widely in manufacturing of diet and reduced calorie food. Although natural caloric sweeteners such as sucrose, fructose, and glucose provide the most desirable taste to consumers, they possess high calorie values. High intensity sweeteners do not affect the blood glucose level and provide little or no nutritive value.

*Stevia rebaudiana* Bertoni is a perennial shrub of the *Asteraceae* (*Compositae*) family native to certain regions of South America. The leaves of the plant contain from 10 to 20% of diterpene glycosides, which are around 150 to 450 times sweeter than sugar. The leaves have been traditionally used for hundreds of years in Paraguay and Brazil to sweeten local teas and medicines.

At present there are more than 230 *Stevia* species with significant sweetening properties. The plant has been successfully grown under a wide range of conditions from its native subtropics to the cold northern latitudes.

The extract of *Stevia rebaudiana* plant contains a mixture of different sweet diterpene glycosides, which have a single base—steviol—and differ by the presence of carbohydrate residues at positions C13 and C19. These glycosides accumulate in *Stevia* leaves and compose approximately 10%-20% of the total dry weight. Typically, on a dry weight basis, the four major glycosides found in the leaves of *Stevia* are Dulcoside A (0.3%), Rebaudioside C (0.6-1.0%), Rebaudioside A (3.8%) and Stevioside (9.1%). Other glycosides identified in *Stevia* extract include Rebaudioside B, C, D, E, and F, Steviolbioside and Rubusoside. Among steviol glycosides only Stevioside and Rebaudioside A are available on a commercial scale.

Steviol glycosides have zero calories and can be used wherever sugar is used. They are ideal for diabetic and low calorie diets. In addition, the sweet steviol glycosides possess functional and sensory properties superior to those of many high potency or high intensity sweeteners.

Rebaudioside D (CAS No: 63279-13-0), as shown in FIG. 1, is one of the sweet glycosides found in *Stevia rebaudiana*. Studies show that highly purified forms of Rebaudioside D possess a very desirable taste profile, almost lacking the bitterness and lingering licorice aftertaste typical for other Steviol glycosides.

These properties multiply the significance of Rebaudioside D and attract great interest for methods of preparation of highly purified forms of Rebaudioside D. However, highly purified steviol glycosides possess relatively low water solubility. For example Rebaudioside A thermodynamic equilibrium solubility at room temperature is only 0.8%.

On the other hand, it is well known that Rebaudioside A exhibits so called polymorphism (Zell T. M., Padden B. E., Grant D. J. W., Schroeder S. A., Wachholder K. L., Prakash I., Munsona E. J. (2000) Investigation of Polymorphism in Aspartame and Neotame Using Solid-State NMR Spectroscopy, Tetrahedron, 56, 6603-6616). Rebaudioside A amorphous, anhydrous and solvate forms differ significantly from each other in terms of solubility, which is one of the main criteria for the commercial viability of a sweetener. In this regard, as shown in Table 1, the hydrate form of Rebaudioside A displays the lowest solubility (Prakash I., DuBois G. E., Clos J. F., Wilkens K. L., Fosdick L. E. (2008) Development of rebiana, a natural, non-caloric sweetener, Food Chem. Toxicol., 46, S75-S82). It was shown that Rebaudioside A may transform from one polymorph form to another at certain conditions (U.S. patent application Ser. No. 11/556,049).

TABLE 1

Properties of Rebaudioside A forms (U.S. patent application Ser. No. 11/556,049)

| | Polymorph Forms | | | |
| --- | --- | --- | --- | --- |
| | Form 1 Hydrate | Form 2 Anhydrous | Form 3 Solvate | Form 4 Amorphous |
| Rate of dissolution in H$_2$O at 25° C. | Very low (<0.2% in 60 minutes) | Intermediate (<30% in 5 minutes) | High (>30% in 5 minutes) | High (>35% in 5 minutes) |
| Alcohol content | <0.5% | <1% | 1-3% | <0.05% |
| Moisture content | >5% | <1% | <3% | 6.74% |

Rebaudioside D possesses even lower water solubility compared to Rebaudioside A. In room temperature it can be dissolved only at 0.05%. When heat is applied, one can make up to 0.5% solution, but upon cooling to room temperature, Rebaudioside D will quickly crystallize back out from the solution. Considering high sweetness intensity of Rebaudioside D, even 0.05% solubility can be sufficient for many applications.

Many food production processes use highly concentrated ingredient mixes prior to producing final forms of food products. In that case, higher concentrations of dissolved Rebaudioside D will be required. It has to be noted that using the heat for dissolution of Rebaudioside D may not be possible in many compositions which contain heat sensitive components. Also maintaining high temperature of mixture for prolonged time to prevent premature crystallization of Rebaudioside D can cause thermal degradation of mixture components or undesirable changes of organoleptic properties.

Therefore there is a need for developing highly soluble forms or compositions of Rebaudioside D which can provide stable solutions with minimal or no heat treatment.

Furthermore, considering the similar chemical structures of Rebaudioside D and other steviol glycosides, as well as other terpene glycosides, the developed approaches may be used in the case of other glycosides as well.

SUMMARY OF THE INVENTION

The invention relates to a process for producing highly soluble compositions containing purified steviol glycosides from *Stevia rebaudiana* Bertoni plant extract, more particularly Rebaudioside D.

Hereinafter the term "steviol glycoside(s)" will mean Rebaudioside A, Rebaudioside B, Rebaudioside C, Rebaudioside D, Rebaudioside E, Rebaudioside F, Stevioside, Steviolbioside, Dulcoside A, Rubusoside, or other glycoside of steviol and combinations thereof.

Hereinafter, unless specified otherwise the solubility of material is determined in RO (reverse osmosis) water at room temperature. Where the solubility is expressed as "%" it to be understood as number of grams of material soluble in 100 grams of solvent.

Hereinafter the term "highly purified" will mean purity level of at least 95% (w/w) on anhydrous basis.

Hereinafter the term "low purity" will mean purity level of less than 95% (w/w) on anhydrous basis.

Hereinafter the term "TSG content" will mean Total Steviol Glycosides content, and it will be calculated as sum of all steviol glycosides' content including Rebaudioside A, Rebaudioside B, Rebaudioside C, Rebaudioside D, Rebaudioside E, Rebaudioside F, Stevioside, Steviolbioside, Dulcoside A and Rubusoside.

Hereinafter the terms "Reb A, B, C, D, E, F" refer to Rebaudiosides A, B, C, D, E, F, respectively.

Hereinafter the term "Reb D" refers to Rebaudioside D (CAS No. 63279-13-0).

Hereinafter the term "crystalline Rebaudioside D" will refer to any form of highly purified Rebaudioside D obtained by crystallization from an aqueous or aqueous alcoholic solution containing Rebaudioside D and further separating the Rebaudioside D crystals and drying them by any means known to the art.

Hereinafter the term "amorphous Rebaudioside D" will refer to any form of highly purified Rebaudioside D obtained by spray drying or freeze drying of aqueous or aqueous alcoholic solution containing Rebaudioside D.

Hereinafter the terms "non-steviol glycoside fraction" or "non-glycoside fraction" will mean materials predominantly comprising compounds, other than steviol glycosides, which are present in the water extracts of Stevia rebaudiana leaves or commercially available stevia extracts at more than 0.0001% (w/w) on dry basis. Not limiting examples of such compounds include typical plant materials, such as pigments and saccharides, phenolic compounds, volatile oil components, sterols, triterpenes, flavonoids, coumarins, non-glycosidic diterpenes (sterebins) spathulenol, decanoic acid, 8,11,14-ecosatrienoic acid, 2-methyloctadecane, pentacosane, octacosane, stigmasterol, bsitosterol, a- and b-amyrine, lupeol, b-amyrin acetate, and pentacyclic triterpene or combinations thereof. The materials designated as "non-steviol glycoside fraction" or "non-glycoside fraction" and prepared in some embodiments of present invention may also contain small residual amounts of steviol glycosides.

Hereinafter the term "polyol" refers to a compound that contains more than one hydroxyl group. A polyol may contain 2 to 7 hydroxyl groups. Non-limiting examples of polyols include erythritol, maltitol, mannitol, sorbitol, lactitol, xylitol, inositol, isomalt, propylene glycol, glycerol (glycerine), threitol, galactitol, reduced isomalto-oligosaccharides, reduced xylo-oligosaccharides, reduced gentio-oligosaccharides, reduced maltose syrup, reduced glucose syrup or combinations thereof.

Hereinafter the term "molasses" refers to sugarcane molasses such as first molasses, second molasses, US grade "A", "B", "C", and substandard blackstrap molasses, as well as beet sugar molasses, boil-back molasses, high-test molasses, refiners' molasses, sweet sorghum syrup. Non-limiting examples of typical constituents of molasses are sucrose, glucose, fructose, starch, gums, pentosans, hexitols, myo-inositols, mannitol, aminoacids, wax, sterols, phosphatides, aconitic, citric, malic, oxalic, glycolic, succinic, fumaric acids, melanoidins or mixtures thereof.

Hereinafter the term "caramel" refers to class I (INS No: 150a), Class II (INS No: 150b) class III (INS No: 150c), and class IV (INS No: 150d) caramel colors or mixtures thereof.

In one embodiment of the invention, crystalline Reb D was dissolved in a water ethanol mixture and spray dried to obtain amorphous form of Reb D with improved solubility.

In another embodiment, crystalline or amorphous Reb D is combined with a polyol at a ratio of 1:100 to 100:1 (w/w) to obtain a composition with improved RebD solubility.

In yet another embodiment, the combination of crystalline Reb D and polyol at a ratio of 1:100 to 100:1 (w/w) is dissolved in water or aqueous alcohol and spray dried to provide a composition with improved Reb D solubility.

In another embodiment, the combination of amorphous Reb D and polyol at a ratio of 1:100 to 100:1 (w/w) is granulated by means of roll compact granulator. The granulated material made in accordance with the present invention advantageously yields a product with favorable characteristics such as Reb D solubility and particle size distribution.

In another embodiment, steviol glycosides are separated from Stevia rebaudiana leaves' water extract to obtain the non-glycoside fraction of Stevia. Any separation technique known to the art, such as chromatographic separation, crystallization from water or aqueous alcohol, adsorption on specific resins, membrane separation, or supercritical fluid extraction may be employed.

In another embodiment, amorphous or crystalline Reb D is combined with a non-glycoside fraction of stevia at a ratio of 1:100 to 100:1 (w/w) to obtain a composition with improved RebD solubility.

In yet another embodiment the combination of crystalline Reb D and non-glycoside fraction of stevia at a ratio of 1:100 to 100:1 (w/w) is dissolved in water or aqueous alcohol and spray dried to provide a composition with improved Reb D solubility.

In another embodiment, amorphous or crystalline Reb D is combined with molasses or caramel at a ratio of 1:100 to 100:1 (w/w) to obtain a composition with improved RebD solubility.

In yet another embodiment, the combination of crystalline Reb D and molasses or caramel at a ratio of 1:100 to 100:1 (w/w) is dissolved in water or aqueous alcohol and spray dried to provide a composition with improved Reb D solubility.

It is to be understood that both the foregoing general description and the following detailed description are exemplary and explanatory and are intended to provide further explanation of the invention as claimed.

BRIEF DESCRIPTION OF THE DRAWING

FIG. 1 shows the chemical structure of Rebaudioside D (CAS No: 63279-13-0).

DETAILED DESCRIPTION OF THE INVENTION

The invention is aimed to provide Rebaudioside D forms or compositions containing Rebaudioside D with improved solubility in water.

In one embodiment, highly purified crystalline Rebaudioside D, which has a solubility of 0.05%, was dissolved in aqueous alcohol at a concentration of 0.5 to 50%, preferably 5-25%, more preferably 10-20%. The alcohol content used in aqueous alcohol is 0.1-100% (vol/vol), preferably 20-70%

(vol/vol), more preferably 30-50% (vol/vol). The alcohol is selected from the group consisting of alkanols, more particularly methanol, ethanol, n-propanol, 2-propanol, 1-butanol, 2-butanol or combinations thereof. To dissolve the Reb D, the solution is heated to 30-100° C., preferably 50-100° C., more preferably 60-100° C. To prevent premature crystallization, the solution is maintained at 20-80° C., preferably 30-70° C., more preferably 50-60° C. The solution is fed to a spray drier to obtain a powder of highly purified amorphous Reb D with a solubility of 0.2%.

In another embodiment highly purified amorphous or crystalline Rebaudioside D is combined with a polyol at a ratio of 1:1 to 1:100 (wt/wt), preferably 1:1 to 1:30 (wt/wt), more preferably 1:1 to 1:10. The polyol is selected from group consisting of erythritol, maltitol, mannitol, sorbitol, lactitol, xylitol, inositol, isomalt, propylene glycol, glycerol (glycerine), threitol, galactitol, reduced isomalto-oligosaccharides, reduced xylo-oligosaccharides, reduced gentio-oligosaccharides, reduced maltose syrup, reduced glucose syrup or combinations thereof. Preferably, the polyol is selected from group consisting of erythritol, maltitol, mannitol, sorbitol, lactitol, xylitol, inositol, and isomalt, and more preferably, erythritol, maltitol, sorbitol, and isomalt. When the prepared compositions containing crystalline Reb D are dissolved in water at room temperature the solubility of Reb D is 0.1-2.0%. For compositions with amorphous RebD the solubility under the same conditions is 0.3-2.0%.

In another embodiment, the combination of amorphous Reb D and polyol at a ratio of 1:1 to 1:100 (w/w), preferably 1:1 to 1:30 (w/w), more preferably 1:1 to 1:10, is granulated by means of any equipment known to art suitable for granulation of fine powder into granules, preferably by means of a roll compact granulator. The roll speed was between about 5-20 rpm, preferably between about 7-10 rpm, and more preferably about 9 rpm. The roll pressure was between about 20-80 bar, preferably between about 40-50 bar, and more preferably about 45 bar. The granulator rotors were rotating at a rate of between about 50-2000 rpm, preferably between about 100-200 rpm, and more preferably at about 150 rpm. The granulators were equipped with screens which sizes were between about 0.5-6.0 mm, preferably between about 1-4 mm, and more preferably about 3.1 mm for the pre-granulator and about 1.6 mm for the fine granulator. When the prepared compositions are dissolved in water, the solubility of Reb D is 0.1-2.5%.

In another embodiment, the non-glycosidic fraction of stevia is combined with crystalline Rebaudioside D, at a ratio of 1:1 to 1:100 (wt/wt), preferably 1:2 to 1:20 (wt/wt), more preferably 1:3 to 1:10. The mixture is dissolved in aqueous alcohol at a concentration of 0.5 to 50%, preferably 5-25%, more preferably 10-20%. The alcohol content in used aqueous alcohol is 0.1-100% (vol/vol), preferably 20-70% (vol/vol), more preferably 30-50% (vol/vol). The alcohol is selected from the group consisting of alkanols, more particularly methanol, ethanol, n-propanol, 2-propanol, 1-butanol, and 2-butanol. To dissolve the Reb D, the solution is heated to 30-100° C., preferably 50-100° C., more preferably 60-100° C. To prevent premature crystallization, the solution is maintained at 20-80° C., preferably 30-70° C., more preferably 50-60° C. The solution is fed to a spray drier to obtain a powder of highly soluble Reb D composition. When the prepared compositions are dissolved in water at room temperature the solubility of Reb D is 0.3-5.0%, or 0.1-2.5%.

In another embodiment, molasses are combined with crystalline Rebaudioside D, at a ratio of 1:1 to 1:100 (w/w), preferably 1:2 to 1:20 (w/w), more preferably 1:3 to 1:10. The mixture is dissolved in aqueous alcohol at a concentration of 0.5 to 50%, preferably 5-25%, more preferably 10-20%. The alcohol content in used aqueous alcohol is 0.1-100% (vol/vol), preferably 20-70% (vol/vol), more preferably 30-50% (vol/vol). The alcohol is selected from the group consisting of alkanols, more particularly methanol, ethanol, n-propanol, 2-propanol, 1-butanol, 2-butanol. The molasses are selected from the group comprising of US grade "A", "B" and "C" molasses as well as substandard molasses, preferably grade "A" molasses. To dissolve the Reb D the solution is heated to 30-100° C., preferably 50-100° C., more preferably 60-100° C. To prevent premature crystallization the solution is maintained at 20-80° C., preferably 30-70° C., more preferably 50-60° C. The solution is fed to a spray drier to obtain a powder of highly soluble Reb D composition. When the prepared compositions are dissolved in water, the solubility of Reb D is 0.1-3.5%.

In another embodiment, caramel is combined with crystalline Rebaudioside D, at a ratio of 1:1 to 1:100 (w/w), preferably 1:2 to 1:20 (w/w), more preferably 1:3 to 1:10. The mixture is dissolved in aqueous alcohol at a concentration of 0.5 to 50%, preferably 5-25%, more preferably 10-20%. The alcohol content in used aqueous alcohol is 0.1-100% (vol/vol), preferably 20-70% (vol/vol), more preferably 30-50% (vol/vol). The alcohol is selected from the group consisting of alkanols, more particularly methanol, ethanol, n-propanol, 2-propanol, 1-butanol, 2-butanol. The caramel is selected from the group comprising of class I, class II, class III and class IV caramel colors, preferably, class I caramel. To dissolve the Reb D the solution is heated to 30-100° C., preferably 50-100° C., more preferably 60-100° C. To prevent premature crystallization the solution is maintained at 20-80° C., preferably 30-70° C., more preferably 50-60° C. The solution is fed to a spray drier to obtain a powder of highly soluble Reb D composition. When the prepared compositions are dissolved in water, the solubility of Reb D is 0.3-3.5%.

The following examples illustrate preferred embodiments of the invention. It will be understood that the invention is not limited to the materials, proportions, conditions and procedures set forth in the examples, which are only illustrative.

EXAMPLE 1

Preparation of Amorphous Rebaudioside D 100 g of crystalline Rebaudioside D, produced by PureCircle Sdn Bhd, with 98.1% purity (on anhydrous basis) was dissolved in 500 mL aqueous ethanol, containing 50% (vol.) ethanol. The solution was maintained at 50° C. and dried using a YC-015 laboratory spray drier (Shanghai Pilotech Instrument & Equipment Co. Ltd., China) operating at 175° C. inlet and 100° C. outlet temperatures. The obtained amorphous powder was compared with crystalline material for solubility.

TABLE 2

Solubility of Rebaudioside D

| Temperature | Solubility, % (in water) | |
|---|---|---|
| | Crystalline | Amorphous |
| 20° C. | 0.05 | 0.1 |
| 50° C.* | 0.2 | 0.5 |
| 100° C.* | 0.5 | 1.1 |

*Solutions obtained at 50° C. and 100° C. crystallized after cooling down to room temperature (20° C.).

EXAMPLE 2

Preparation of Non-Glycosidic Stevia Fraction 500 g of commercial stevia extract, containing Rebaudioside A 41.2%, Stevioside 30.6%, Rebaudioside C 9.9%, Rebaudioside F 2.3%, Dulcoside A 0.5%, Rubusoside 0.6%, Rebaudioside D 1.5%, Steviolbioside 0.2% and Rebaudioside B 0.1% were dissolved in 9.5 liter of RO water and passed through a column packed with 10 liter Amberlite XAD7HP resin. The column was washed with 10 volumes of RO water. The collected water fractions were evaporated under vacuum at 55° C. and spray dried to yield 45 g powder with 9.8% TSG including 7.8% Rebaudioside D, 2.0% Rebaudioside A and non-detectable amounts of other steviol glycosides.

EXAMPLE 3

Preparation of Rebaudioside D Soluble Composition 10 g of crystalline Rebaudioside D, produced by PureCircle Sdn Bhd, with 98.1% purity (on anhydrous basis) was mixed with different amounts of erythritol (Prima Inter-Chem Sdn Bhd, Malaysia). The obtained blends were tested for solubility, and solution stability to crystallization, during storage at room temperature.

TABLE 3

Solubility of Rebaudioside D blends

| Blend ratio, wt/wt | Solubility*, % (RebD in water) | |
| --- | --- | --- |
| RebD/Erythritol | 20° C. | 100° C.** |
| 2:1 | 0.06 | 0.09 |
| 1:1 | 0.08 | 0.2 |
| 1:5 | 0.2 | 0.5 |
| 1:10 | 0.4 | 1.0 |
| 1:15 | 0.8 | 1.3 |
| 1:20 | 1.5 | 2.0 |

*Solubility is calculated for RebD % content in solution
**The material was dissolved at 100° C. and cooled down to room temperature (20° C.). The reported concentrations are stable (do not crystallize) for 24 hrs storage in room temperature.

EXAMPLE 4

Preparation of Rebaudioside D Soluble Composition 10 g of amorphous Rebaudioside D prepared according to EXAMPLE 1, was mixed with different amounts of erythritol (Prima Inter-Chem Sdn Bhd, Malaysia). The obtained blends were tested for solubility, and solution stability to crystallization, during storage at room temperature.

TABLE 4

Solubility of Rebaudioside D blends

| Blend ratio, wt/wt | Solubility*, % (RebD in water) | |
| --- | --- | --- |
| RebD/Erythritol | 20° C. | 100° C.** |
| 2:1 | 0.08 | 0.09 |
| 1:1 | 0.16 | 0.2 |
| 1:5 | 0.4 | 0.5 |
| 1:10 | 0.9 | 1.0 |
| 1:15 | 1.0 | 1.3 |
| 1:20 | 1.1 | 2.0 |

*Solubility is calculated for RebD % content in solution
**The material was dissolved at 100° C. and cooled down to room temperature (20° C.). The reported concentrations are stable (do not crystallize) for 24 hrs storage in room temperature.

EXAMPLE 5

Preparation of Rebaudioside D Soluble Composition 10 g of crystalline Rebaudioside D, produced by PureCircle Sdn Bhd, with 98.1% purity (on anhydrous basis) was mixed with different amounts of erythritol (Prima Inter-Chem Sdn Bhd, Malaysia). The obtained blends were dissolved in 5 volumes of aqueous ethanol, containing 50% (vol.) ethanol. The solution was maintained at 50° C. and dried using a YC-015 laboratory spray drier (Shanghai Pilotech Instrument & Equipment Co. Ltd., China) operating at 175° C. inlet and 100° C. outlet temperatures. The obtained amorphous powder was tested for solubility, and solution stability to crystallization, during storage at room temperature.

TABLE 5

Solubility of Rebaudioside D blends

| Blend ratio, wt/wt | Solubility*, % (RebD in water) | |
| --- | --- | --- |
| RebD/Erythritol | 20° C. | 100° C.** |
| 2:1 | 0.16 | 0.2 |
| 1:1 | 0.3 | 0.4 |
| 1:5 | 0.6 | 0.7 |
| 1:10 | 1.2 | 1.4 |
| 1:15 | 1.5 | 1.8 |
| 1:20 | 1.8 | 2.5 |

*Solubility is calculated for RebD % content in solution
**The material was dissolved at 100° C. and cooled down to room temperature (20° C.). The reported concentrations are stable (do not crystallize) for 24 hrs storage in room temperature.

EXAMPLE 6

Preparation of Rebaudioside D Soluble Composition 10 g of crystalline Rebaudioside D, produced by PureCircle Sdn Bhd, with 98.1% purity (on anhydrous basis) was mixed with different amounts of stevia non-glycosidic fraction prepared according to EXAMPLE 2. The obtained blends were tested for solubility, and solution stability to crystallization, during storage at room temperature.

TABLE 6

Solubility of Rebaudioside D blends

| Blend ratio, wt/wt | Solubility*, % (RebD in water) | |
| --- | --- | --- |
| RebD/Non-glyc. fraction | 20° C. | 100° C.** |
| 1:2 | 0.07 | 2.1 |
| 1:1 | 0.06 | 1.5 |
| 2:1 | 0.06 | 1.3 |

TABLE 6-continued

Solubility of Rebaudioside D blends

| Blend ratio, wt/wt | Solubility*, % (RebD in water) | |
| --- | --- | --- |
| RebD/Non-glyc. fraction | 20° C. | 100° C.** |
| 3:1 | 0.06 | 0.8 |
| 4:1 | 0.06 | 0.3 |
| 5:1 | 0.05 | 0.15 |

*Solubility is calculated for RebD % content in solution
**The material was dissolved at 100° C. and cooled down to room temperature (20° C.). The reported concentrations are stable (do not crystallize) for 24 hrs storage in room temperature.

EXAMPLE 7

Preparation of Rebaudioside D Soluble Composition 10 g of amorphous Rebaudioside D, prepared according to EXAMPLE 1, was mixed with different amounts of stevia non-glycosidic fraction, prepared according to EXAMPLE 2. The obtained blends were tested for solubility, and solution stability to crystallization, during storage at room temperature.

TABLE 7

Solubility of Rebaudioside D blends

| Blend ratio, wt/wt | Solubility*, % (RebD in water) | |
| --- | --- | --- |
| RebD/Non-glyc. fraction | 20° C. | 100° C.** |
| 1:2 | 0.1 | 2.1 |
| 1:1 | 0.09 | 1.5 |
| 2:1 | 0.08 | 1.3 |
| 3:1 | 0.06 | 0.8 |
| 4:1 | 0.06 | 0.3 |
| 5:1 | 0.05 | 0.15 |

*Solubility is calculated for RebD % content in solution
**The material was dissolved at 100° C. and cooled down to room temperature (20° C.). The reported concentrations are stable (do not crystallize) for 24 hrs storage in room temperature.

EXAMPLE 8

Preparation of Rebaudioside D Soluble Composition 10 g of crystalline Rebaudioside D was mixed with different amounts of stevia non-glycosidic fraction, prepared according to EXAMPLE 2. The obtained blends were dissolved in 5 volumes of aqueous ethanol, containing 50% (vol.) ethanol. The solution was maintained at 50° C. and dried using a YC-015 laboratory spray drier (Shanghai Pilotech Instrument & Equipment Co. Ltd., China) operating at 175° C. inlet and 100° C. outlet temperatures. The obtained amorphous powder was tested for solubility, and solution stability to crystallization, during storage at room temperature.

TABLE 8

Solubility of Rebaudioside D blends

| Blend ratio, wt/wt | Solubility*, % (RebD in water) | |
| --- | --- | --- |
| RebD/Non-glyc. fraction | 20° C. | 100° C.** |
| 1:2 | 0.4 | 2.5 |
| 1:1 | 0.3 | 2.1 |

TABLE 8-continued

Solubility of Rebaudioside D blends

| Blend ratio, wt/wt | Solubility*, % (RebD in water) | |
| --- | --- | --- |
| RebD/Non-glyc. fraction | 20° C. | 100° C.** |
| 2:1 | 0.2 | 1.8 |
| 3:1 | 0.1 | 1.4 |
| 4:1 | 0.08 | 0.9 |
| 5:1 | 0.06 | 0.4 |

*Solubility is calculated for RebD % content in solution
**The material was dissolved at 100° C. and cooled down to room temperature (20° C.). The reported concentrations are stable (do not crystallize) for 24 hrs storage in room temperature

EXAMPLE 9

Preparation of Rebaudioside D Soluble Composition 10 g of crystalline Rebaudioside D, produced by PureCircle Sdn Bhd, was mixed with different amounts of molasses (Chee Lam Trading, Malaysia). The obtained blends were dissolved in 5 volumes of aqueous ethanol, containing 50% (vol.) ethanol. The solution was maintained at 50° C. and dried using a YC-015 laboratory spray drier (Shanghai Pilotech Instrument & Equipment Co. Ltd., China) operating at 175° C. inlet and 100° C. outlet temperatures. The obtained amorphous powder was tested for solubility, and solution stability to crystallization, during storage at room temperature.

TABLE 9

Solubility of Rebaudioside D blends

| Blend ratio, w/w | Solubility*, % (RebD in water) | |
| --- | --- | --- |
| RebD/Molasses | 20° C. | 100° C.** |
| 1:2 | 0.5 | 3.5 |
| 1:1 | 0.3 | 2.6 |
| 2:1 | 0.2 | 2.1 |
| 3:1 | 0.1 | 1.6 |
| 4:1 | 0.09 | 1.2 |
| 5:1 | 0.08 | 0.5 |

*Solubility is calculated for RebD % content in solution
**The material was dissolved at 100° C. and cooled down to room temperature (20° C.). The reported concentrations are stable (do not crystallize) for 24 hrs storage in room temperature

EXAMPLE 10

Preparation of Granulated Rebaudioside D Soluble Composition 1 kg of amorphous Rebaudioside D prepared according to EXAMPLE 1, was mixed with different amounts of erythritol (Prima Inter-Chem Sdn Bhd, Malaysia). The obtained blends were transferred to an Alexanderwerk WP 50N/75 roller compactor. The compactor was operating at 9 rpm and 45 bar pressure. The compacted mass was fed to a pre-granulator and a fine granulator with rotors at rotating at 150 rpm. The screen size for the pre-granulator was 3.1 mm and for the fine granulator was 1.6 mm. The "overs" (particles that are too large) and "fines" (particles that are too small) were separated by top screen having a screen size of US Mesh 10 and bottom screen of US Mesh 40. The % ratio of "overs":"product": "fines" was 0.9%:78.2%:20.9% respectively. The obtained products were tested for solubility, and solution stability to crystallization, during storage at room temperature.

TABLE 10

Solubility of Rebaudioside D blends

| Blend ratio, w/w | Solubility*, % (RebD in water) | |
| --- | --- | --- |
| RebD/Erythritol | 20° C. | 100° C.** |
| 2:1 | 0.09 | 0.1 |
| 1:1 | 0.17 | 0.2 |
| 1:5 | 0.4 | 0.6 |
| 1:10 | 0.9 | 1.2 |
| 1:15 | 1.0 | 1.8 |
| 1:20 | 1.5 | 2.5 |

*Solubility is calculated for RebD % content in solution
**The material was dissolved at 100° C. and cooled down to room temperature (20° C.). The reported concentrations are stable (do not crystallize) for 24 hrs storage in room temperature While the foregoing has described one or more embodiments of the present invention, it will be understood by those skilled in the art that various changes and modifications may be made and equivalents may be substituted for elements or compositions thereof without departing from the true scope of the invention. Therefore, it is intended that this invention not be limited to a particular embodiment disclosed, but that the invention will include all embodiments falling within the scope of the appended claims.

The invention claimed is:

1. A method of preparing a highly soluble Rebaudioside D composition, comprising the steps of:
    a. providing a first composition comprising Rebaudioside D;
    b. providing a second composition comprising at least one component selected from the group consisting of: a non-glycosidic fraction of *Stevia*; molasses; and caramel color;
    c. dissolving the first and second compositions in a solvent selected from the group consisting of water or aqueous alcohol to make a solution; and
    d. spray drying the solution to obtain the highly soluble Rebaudioside D composition, wherein said Rebaudioside D composition has a water solubility of at least about 0.05% at 20°C.

2. The method of claim 1 wherein the second composition comprises a non-glycosidic fraction of *Stevia* at a ratio (wt/wt) of the non-glycosidic fraction of *Stevia* to the first composition of about 1:100 to about 100:1, preferably about 1:2 to about 1:20, more preferably about 1:3 to about 1:10.

3. The method of claim 2 wherein the non-glycosidic fraction of *Stevia* is prepared by a process comprising the steps of:
    providing a stevia extract;
    dissolving the stevia extract in water or aqueous alcohol to form a stevia extract solution;
    passing the stevia extract solution through a chromatographic system packed with macroporous adsorbent resin capable of adsorbing steviol glycosides;
    collecting an effluent from the chromatographic system; and
    drying the effluent to obtain the non-glycosidic fraction of *Stevia*.

4. The method of claim 3, wherein the *stevia* extract contains about 10-95%, preferably about 30-90%, and more preferably about 40-85% total steviol glycosides.

5. The method of claim 3, wherein the water or aqueous alcohol ratio to dissolved *stevia* extract solids (vol/wt) is about 1:1 to about 200:1, preferably about 5:1 to about 100:1, more preferably about 10:1 to about 50:1.

6. The method of claim 3 wherein the amount of *stevia* extract exceeds an adsorption capacity of the adsorbent in the chromatographic system by about 1-10 times, preferably by about 1-5 times, and more preferably by about 1-1.5 times.

7. The method of claim 3, wherein the chromatographic system comprises about 1-20 consecutively connected columns, preferably about 1-10 columns, and more preferably about 1-6 columns.

8. The method of claim 1, wherein the second composition comprises molasses at a ratio (w/w) of molasses to the first composition of about 1:100 to about 100:1, preferably about 1:2 to about 1:20 and more preferably about 1:3 to about 1:10.

9. The method of claim 8, wherein the molasses is selected from the group consisting of: sugarcane molasses such as first molasses, second molasses, US grade "A", "B", "C", and substandard blackstrap molasses; beet sugar molasses; boilback molasses; high-test molasses; refiners' molasses; sweet sorghum syrup; and a combination thereof.

10. The method of claim 1, wherein the second composition comprises caramel at a ratio (w/w) of caramel to the first composition of about 1:100 to about 100:1, preferably about 1:2 to about 1:20, and more preferably about 1:3 to about 1:10.

11. The method of claim 10, wherein the caramel is selected from the group consisting of Class I (INS No: 150*a*), Class II (INS No: 150*b*), Class III (INS No: 150*c*), and Class IV (INS No: 150*d*) caramel colors and combinations thereof.

12. The method of claim 1, wherein the drying step comprises spray drying the solution in a spray drier operating at an inlet temperature of about 150-200° C. and an outlet temperature of about 80-120° C.

* * * * *